United States Patent
Yada et al.

(10) Patent No.: US 7,892,403 B2
(45) Date of Patent: Feb. 22, 2011

(54) HANDLING DEVICE AND PRODUCING SYSTEM OF EASY-TO-POLYMERIZE COMPOUND

(75) Inventors: Shuhei Yada, Minato-ku (JP); Yasushi Ogawa, Yokkaichi (JP); Yoshiro Suzuki, Yokkaichi (JP); Kimikatsu Jinno, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1132 days.

(21) Appl. No.: 11/578,237

(22) PCT Filed: Sep. 7, 2004

(86) PCT No.: PCT/JP2004/012979
§ 371 (c)(1),
(2), (4) Date: Oct. 12, 2006

(87) PCT Pub. No.: WO2005/110949
PCT Pub. Date: Nov. 24, 2005

(65) Prior Publication Data
US 2008/0271984 A1    Nov. 6, 2008

(30) Foreign Application Priority Data
May 17, 2004 (JP) .............................. 2004-146169

(51) Int. Cl.
*B01D 5/00* (2006.01)
*C07C 51/44* (2006.01)
*C07C 67/54* (2006.01)
*C07C 69/54* (2006.01)

(52) U.S. Cl. .................... 202/182; 202/185.1; 202/194; 202/195; 202/262; 202/266; 203/8; 203/9; 203/90; 203/DIG. 21; 560/218; 562/600

(58) Field of Classification Search ............ 159/3, 159/48.1; 202/182, 185.1, 194, 195, 262, 202/266; 203/8, 9, 90, DIG. 21; 560/218; 562/600
See application file for complete search history.

(56) References Cited

U.S. PATENT DOCUMENTS
6,294,056 B1 * 9/2001 Matsumoto et al. ........... 203/90

(Continued)

FOREIGN PATENT DOCUMENTS
JP     11 269128     10/1999

(Continued)

OTHER PUBLICATIONS
Distillation Engineering Handbook, 1966, p. 423 (with English translation).

*Primary Examiner*—Virginia Manoharan
(74) *Attorney, Agent, or Firm*—Oblon, Spivak, McClelland, Maier & Neustadt, L.L.P.

(57) ABSTRACT

A condenser includes: a top face of a tube plate on which acrylic acid may be condensed inside the condenser; a spray for spreading a polymerization inhibitor on the tube plate; a first polymerization inhibitor supply tube for supplying the polymerization inhibitor to the spray; and a supporter for supporting the spray at a predetermined position. The supporter supports the first polymerization inhibitor supply tube outside the condenser. The condenser allows a stable continuous operation for a long period of time by preventing polymerization of an easily polymerizable compound in the condenser into which a vapor of an easily polymerizable compound is supplied with a simple structure thereof.

16 Claims, 6 Drawing Sheets

U.S. PATENT DOCUMENTS

| | | | |
|---|---|---|---|
| 6,409,886 B1 * | 6/2002 | Matsumoto et al. | 203/8 |
| 6,596,129 B1 * | 7/2003 | Yoneda et al. | 203/2 |
| 6,878,239 B1 * | 4/2005 | Matsumoto et al. | 203/8 |
| 7,351,310 B2 * | 4/2008 | Thiel et al. | 203/8 |

FOREIGN PATENT DOCUMENTS

| | | |
|---|---|---|
| JP | 2000 344688 | 12/2000 |
| JP | 2002 179618 | 6/2002 |
| RU | 2 205 820 C2 | 6/2003 |
| SU | 496286 | 12/1975 |

* cited by examiner

HANDLING DEVICE AND PRODUCING SYSTEM OF EASY-TO-POLYMERIZE COMPOUND

TECHNICAL FIELD

The present invention relates to: a device for handling an easily polymerizable compound, applied to column equipment such as a distillation column and an evaporation column for an easily polymerizable compound; and an apparatus for manufacturing an easily polymerizable compound. The present invention more specifically relates to: a device for handling an easily polymerizable compound, applied to column equipment provided with a column top gas condenser or a vent gas condenser; and an apparatus for manufacturing an easily polymerizable compound.

BACKGROUND ART

Equipment for manufacturing an easily polymerizable compound such as (meth)acrylic acid or (meth)acrylate employs column equipment such as a distillation column for crude (meth)acrylic acid or crude (meth)acrylate or a decomposition reaction distillation column for recovering (meth)acrylic acid or the like by decomposing a high boiling point substance.

In such column equipment, part or whole of a column top gas may be cooled and liquefied in a column top gas condenser for liquefaction, to thereby form a reflux or a distillate. Further, a gas (vent gas) containing valuable substances, which were not condensed in the column top gas condenser, may be cooled in a vent gas condenser, to thereby recover the valuable substances.

When a gaseous easily polymerizable substance is condensed and liquefied in a condenser, an inhibitor-less solution without a polymerization inhibitor is formed. Thus, such a condenser for handling an easily polymerizable substance conventionally employs a technique of spraying a solution containing a polymerization inhibitor into the condenser for suppressing formation of a polymerized product in a condensate, to thereby include the polymerization inhibitor in the condensate (see JP 2000-344688 A, for example).

When such a conventional spray for spraying a solution containing a polymerization inhibitor is provided, a tube for introducing a solution containing the polymerization inhibitor into the spray is provided with a supporter for suppressing vibration of the tube and the spray in use because of a volume of liquid flow, a weight of the tube, or the like.

In a conventional vertical fixed tube plate-type condenser 50 to which a gas containing an easily polymerizable compound is supplied from above as shown in FIG. 5 for example, a polymerization inhibitor supply tube 53 which supplies a polymerization inhibitor to a spray 52 such that the polymerization inhibitor is sprayed on an entire top face of a tube plate 51, which is dividing a gas passage and a cooling medium passage, above the tube plate 51 from the spray 52; is supported inside the condenser 50 from below by a supporter 54. Further as shown in FIG. 6 for example, the polymerization inhibitor supply tube 53 is supported by a supporter 55 from above inside the condenser 50. A gas supplied to the condenser 50 is condensed in a cooling tube 56.

A condensate easily forms a polymerized product because the condensate contains no polymerization inhibitor. Thus, a polymerization inhibitor-containing liquid is sprayed on the tube plate 51 from the spray 52 through the polymerization inhibitor supply tube 53 for suppressing polymerization. Thus, formation of a polymerized product on the tube plate 51 is prevented. Further, the polymerization inhibitor-containing liquid flows into the cooling tube 56, to thereby supply the polymerization inhibitor to the condensate formed inside the cooling tube 56.

The above-mentioned conventional condenser is generally provided inside a condenser to avoid interference with a transportation operation or disassembly and cleaning operation of the condenser. However, an easily polymerizable compound may be condensed on a supporter, thereby a polymerized product may be formed.

To be more specific, a temperature of a liquid flowing through the polymerization inhibitor supply tube 53 being in contact with the supporter 54 or 55 is usually lower than a temperature of a gas containing an easily polymerizable compound supplied to the condenser 50. Thus, the supporter 54 or 55 is cooled and a condensate without a polymerization inhibitor is formed on the supporter 54 or 55, possibly a polymerized product may be formed.

DISCLOSURE OF THE INVENTION

An object of the present invention is to provide a device allowing a stable continuous operation with a condenser for a long period of time by preventing polymerization of an easily polymerizable compound in the condenser into which a vapor of an easily polymerizable compound vapor is supplied with a simple structure thereof.

The inventors of the present invention have studied intensively and have found out that formation of a polymerized product can be avoided as follows. (1) The supporter is provided outside a condenser where a condensate is not formed. (2) In case strength is insufficient when the supporter was provided outside the condenser, it is necessary to provide the supporter inside the condenser. In case of providing the supporter inside the condenser, a solution containing a polymerization inhibitor is sprayed on the supporter, too.

That is, the present invention is: a handling device for handling an easily polymerizable compound into which a vapor of an easily polymerizable compound is supplied, comprising: a condensation part in which the easily polymerizable compound may be condensed inside the handling device; a spreader for the condensation part for spreading a polymerization inhibitor on the condensation part; a polymerization inhibitor supply tube for supplying the polymerization inhibitor to the spreader for the condensation part; and a support means for supporting the spreader for the condensation part at a predetermined position inside the handling device, wherein the support means is a means for supporting the polymerization inhibitor supply tube outside the handling device; and an apparatus for manufacturing an easily polymerizable compound having the handling device.

BEST MODE FOR CARRYING OUT THE INVENTIONS

Figure 1:
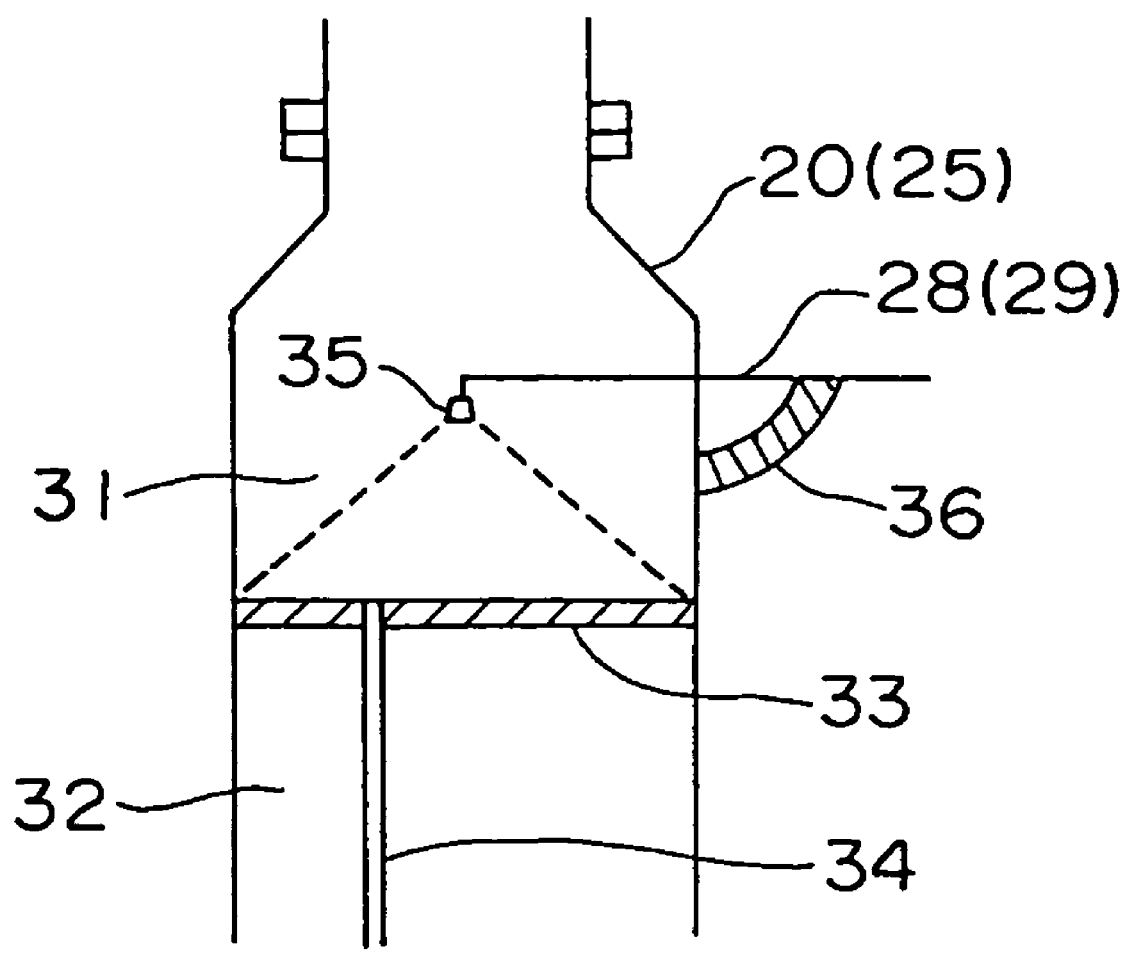
FIG. 1 is a vertical sectional view of an upper portion of a condenser according to an embodiment of the present invention.

Hereinafter, the present invention will be described in more detail.

A handling device for handling an easily polymerizable compound according to the present invention is a device for handling an easily polymerizable compound into which a vapor of an easily polymerizable compound is supplied and comprises: a condensation part in which the easily polymerizable compound may be condensed inside the handling device; a spreader for the condensation part for spreading a polymerization inhibitor in the condensation part; a polymerization inhibitor supply tube for supplying the polymerization inhibitor to the spreader for the condensation part; and a support means for supporting the spreader for the condensation part at a predetermined position inside the handling device, in which (1) the support means is a means for supporting the polymerization inhibitor supply tube outside the handling device or (2) the support means is a means for supporting the polymerization inhibitor supply tube inside the handling device, and the handling device further comprises a spread means for the support means for spreading the polymerization inhibitor to the support means.

The easily polymerizable compound used in the present invention is not particularly limited as long as the compound easily causes a polymerization reaction under conditions such as heat. A typical easily polymerizable compound of the present invention is at least one of the compound selected from acrylic acid, methacrylic acid, and esters thereof. Examples of acrylates include methyl acrylate, ethyl acrylate, butyl acrylate, isobutyl acrylate, t-butyl acrylate, 2-ethylhexyl acrylate, 2-hydroxyethyl acrylate, 2-hydroxypropyl acrylate, and methoxyethyl acrylate. Examples of methacrylates include similar compounds to the above acrylates.

The handling device is not particularly limited as long as a vapor of an easily polymerizable compound is supplied into the device. A substance partially containing the vapor of an easily polymerizable compound or the vapor of an easily polymerizable compound itself may be supplied to the handling device. Examples of such a handling device include a condenser, a distillation column, a tank, a pump, and a tube.

The condensation part is not particularly limited as long as it is a part inside the handling device where a vapor of an easily polymerizable compound may be cooled and where a liquid of an easily polymerizable compound without a polymerization inhibitor may exist. Such a condensation part includes a part whose temperature may be to a lower temperature than that of a vapor of an easily polymerizable compound where a condensate of the easily polymerizable compound tends to accumulate. Examples of such a condensation part include: a tube plate or cooling tube of a condenser; a column top part or trays in the vicinity thereof in a distillation column; an end part in a tank; and an elbow part or a valve provided in a pump or tube.

The present invention is more effectively applied to a handling device in which a liquid of an easily polymerizable compound without a polymerization inhibitor easily forms through condensation of a vapor of an easily polymerizable compound. Examples of such a handling device include a known condenser (heat exchanger) in which a cooling medium passage for a flow of a cooling medium and a passage for a gas containing a vapor of an easily polymerizable compound are divided by a heat transmitting member.

The spreader for the condensation part is not particularly limited as long as it is a device for spreading a polymerization inhibitor in the condenser. Examples of such a spreader for a condenser include a water spray such as a water spray nozzle and a spray such as a spray nozzle. The spray is preferably used in the present invention in terms of a large spreading area and prevention of excess spreading of the polymerization inhibitor.

The polymerization inhibitor supply tube is not particularly limited as long as it is a tube for supplying a polymerization inhibitor to a spreader for the condensation part. Such a polymerization inhibitor supply tube may employ a known tube selected depending on the conditions such as an environment in the handling device and a supply amount of the polymerization inhibitor.

The polymerization inhibitor used in the present invention is not particularly limited as long as the inhibitor suppresses formation of a polymerized product of the easily polymerizable compound. Examples of such a polymerization inhibitor include copper acrylate, copper dithiocarbamate, a phenol compound, and a phenothiazine compound.

Examples of copper dithiocarbamate include: copper dialkyldithiocarbamates such as copper dimethyldithiocarbamate, copper diethyldithiocarbamate, copper dipropyldithiocarbamate, and copper dibutyldithiocarbamate; copper cycloalkylene dithiocarbamates such as copper ethylene dithiocarbamate, copper tetramethylene dithiocarbamate, copper pentamethylene dithiocarbamate, and copper hexamethylene dithiocarbamate; and copper cycloxydialkylene dithiocarbamates such as copper oxydiethylene dithiocarbamate.

Examples of the phenol compound include hydroquinone, methoquinone, pyrogallol, catechol, resorcin, phenol, and cresol.

Examples of the phenothiazine compound include phenothiazine, bis-(α-methylbenzyl)phenothiazine, 3,7-dioctylphenothiazine, and bis-(α-dimethylbenzyl)phenothiazine.

The polymerization inhibitor used in the present invention is selected depending on the conditions such as a type of an easily polymerizable compound. The polymerization inhibitor may be used as it is or as a solution of an easily polymerizable compound to be handled or a solvent not affecting the handling of the easily polymerizable compound such as another appropriate solvent, for the spreading. The polymerization inhibitor to be spread may contain a substance other than those described above depending on processes, but the type or amount thereof may be selected on the condition that the substance does not affect the handling of the easily polymerizable compound.

The support means is not particularly limited as long as it is a means for supporting the polymerization inhibitor supply tube such that the spreader for the condensation part is supported at a predetermined position inside the handling device. Such a means may employ a known means for supporting a tube such as a crossarm, a brace, or a strap. The phrase "predetermined position inside the handling device" refers to a position where the spreader for the condensation part can spread the polymerization inhibitor on the entire condensation part.

The spread means for the support means is not particularly limited as long as it is a means for spreading a polymerization inhibitor on the entire support means provided inside the handling device. Such a spread means for the support means may consist of the above-mentioned spreader or spray and a tube for supplying the polymerization inhibitor thereto.

The present invention provides a manufacturing apparatus for manufacturing an easily polymerizable compound comprising the above-mentioned handling device. The manufacturing apparatus is not particularly limited as long as the apparatus includes the handling device and is capable of manufacturing an easily polymerizable compound. Such a manufacturing apparatus may employ an apparatus usually used in production of an easily polymerizable compound.

The easily polymerizable compound may be manufactured through a known method of producing. Examples of a method of producing acrylic acid and acrylate include the following (1) to (3).

(1) A method includes: an oxidation step for producing acrylic acid through vapor phase catalytic oxidation of propane, propylene, and/or acrolein; a collecting step for collecting acrylic acid as an aqueous solution of acrylic acid by making a gas containing acrylic acid formed in the oxidation step be in contact with water; an extraction step for extracting acrylic acid by using an appropriate extracting solvent from the aqueous solution of acrylic acid obtained in the collecting step; a separation step for separating the acrylic acid and the solvent from the obtained extracted liquid; a purification step for purifying the separated acrylic acid through distillation or the like; a recovery step for recovering valuable substances by supplying as a raw material, a high boiling point liquid containing Michael adducts of acrylic acid and a polymerization inhibitor used in each of the steps recovered from the above-mentioned steps to a decomposition reaction column; and a recycle step for supplying the recovered valuable substances to any step after the collecting step.

(2) A method includes: an oxidation step for producing acrylic acid through vapor phase catalytic oxidation of propane, propylene, and/or acrolein; a collecting step for collecting acrylic acid as an aqueous solution of acrylic acid by making a gas containing acrylic acid formed in the oxidation step be in contact with water; an azeotropic separation step for taking out crude acrylic acid from a bottom of an azeotropic separation column by distilling the aqueous solution of acrylic acid obtained in the collecting step in the azeotropic separation column in the presence of an azeotropic solvent; an acetic acid separation step for removing acetic acid from the acrylic acid taken out; a purification step for removing high boiling point impurities; a recovery step for recovering valuable substances by supplying as a raw material, a high boiling point liquid containing Michael adducts of acrylic acid and a polymerization inhibitor used in each of the steps recovered from the above-mentioned steps to a decomposition reaction column; and a recycle step for supplying the valuable substances to any step after the collecting step.

(3) A method includes: an oxidation step for producing acrylic acid through vapor phase catalytic oxidation of propane, propylene, and/or acrolein; a collecting/separation step for collecting acrylic acid as an organic solution of acrylic acid by making a gas containing acrylic acid formed in the oxidation step be in contact with an organic solvent and simultaneously removing water, acetic acid, and the like; a separation step for taking out the acrylic acid from the organic solution of acrylic acid; a recovery step for recovering valuable substances by supplying as a raw material, a high boiling point liquid containing a polymerization inhibitor and an organic solvent used in each of the steps and Michael adducts of acrylic acid recovered from the above-mentioned steps to a decomposition reacting column; a recycle step for supplying the valuable substances to any step after the collecting step; and a solvent purification step for purifying part or whole of the recovered organic solvent.

A method of producing acrylate includes, for example: an esterification reaction step involving a reaction of acrylic acid and an alcohol with an organic acid, a cationic ion exchange resin, or the like as a catalyst; a concentration step involving extraction, evaporation, and distillation as unit operations for concentrating a solution of crude acrylate obtained through the esterification reaction; a purification step for purifying in a purification column, the acrylate in the concentrated liquid obtained in the concentration step; and a recovery step for recovering valuable substances by supplying to a decomposition reaction column or returning to the process, a high boiling point liquid containing acrylates and Michael adducts such as $\beta$-acryloxypropionates, $\beta$-alkoxypropionates, and $\beta$-hydroxypropionates as main components, in a bottom liquid of the purification column, and polymerization inhibitors used in the above-mentioned steps. Each of the unit operations in the concentration step is arbitrarily selected depending on a raw material ratio of the acrylic acid and the alcohol in the esterification reaction, the catalyst used in the esterification reaction, the physical properties of the raw material, by-products of the reaction, and the acrylates, or the like.

A high boiling point liquid may contain: acrylic acid, an acrylic acid dimer (hereinafter, referred to as a dimer), an acrylic acid trimer (hereinafter, referred to as a trimer), $\beta$-alkoxypropionic acids, and $\beta$-alkoxypropionates as main components, obtained in any step of the steps except in the bottom of the purification column of acrylate products; and polymerization inhibitors used in the production steps, depending on the alcohol used. Valuable substances can be recovered from such a high boiling point liquid, too, by supplying the high boiling point liquid containing Michael adducts to the decomposition reactor. Then, the recovered valuable substances can be supplied to appropriate steps such as the esterification reaction step and the concentration step.

The above-mentioned Michael adduct of acrylic acid or acrylate refers to a product obtained through Michael condensation of acrylic acid and raw materials of acrylate. Examples of such a Michael adduct obtained in production of acrylic acid include: an acrylic acid dimer (hereinafter, referred to as a dimer); an acrylic acid trimer (hereinafter, referred to as a trimer); and an acrylic acid tetramer (hereinafter, referred to as a tetramer). Further, examples of a Michael adduct obtained in production of acrylate include: Michael adducts of acrylic acid to the above-mentioned acrylate such as an alkyl ester having 2 to 8 carbon atoms or a cycloalkyl ester such as $\beta$-acryloxypropionate; Michael adducts of an alcohol such as $\beta$-alkoxypropionate; dimers; trimers; tetramers; esters of trimers; esters of tetramers; $\beta$-hydroxypropionic acid; and $\beta$-hydroxypropionates.

The manufacturing apparatus according to the present invention may employ a device or apparatus usually used in production of an easily polymerizable compound such as a distillation apparatus or evaporation apparatus for an easily polymerizable compound.

The distillation column generally used in a chemical plant may be employed. Trays or packing is provided inside the distillation column. Specific examples of trays include bubble cap trays each having a downcomer, perforated-plate trays, valve trays, SUPERFRAC trays, MAX-FRAC trays, and dual flow trays without downcomers.

Examples of structured packing include: SULZER PACKING available from Sulzer Brothers Ltd.; SUMITOMO-SULZER PACKING available from Sumitomo Heavy Industries, Ltd.; MELLAPAK available from Sumitomo Heavy Industries, Ltd.; GEM-PAK available from Koch-Glitsch, LP; MONTZ-PAK available from Julius Montz GmbH; GOOD ROLL PACKING available from Tokyo Tokushu Kanaami K. K.; HONEYCOMB PACK available from NGK Insulators, Ltd.; IMPULSE PACKING available from Nagaoka International Corporation; and MC PACK available from Mitsubishi Chemical Engineering Corporation.

Examples of random packing include: INTALOX SADDLES available from Saint-Gobain NorPro; TELLER-ETT available from Nittetsu Chemical Engineering Ltd.; PALL RINGS available from BASF Aktiengesellschaft; CASCADE MINI-RING available Mass Transfer Ltd.; and FLEXI RINGS available from JGC Corporation.

The type of the tray and packing is not limited in the present invention, and one type each of the tray and packing can be used, or two or more thereof may be used in combination as generally used. In production of an easily polymerizable compound, a reaction may be carried out in a distillation column, and the reaction distillation column corresponds to the distillation column in the present invention.

The evaporation apparatus generally used in a chemical plant may be employed, too. That is, the evaporation apparatus is provided with an evaporator and a reboiler and may optionally include a condenser (cooler) for condensing an evaporated gas, a tank for storing a condensate, a pump for delivering the condensate, and a vent gas condenser for further cooling an uncondensed gas again. The evaporation apparatus is not particularly limited as long as the apparatus includes the above-mentioned handling device.

A condenser which is a heat exchanger for cooling a column top gas and a condenser which is a heat exchanger for cooling a vent gas are attached to each distillation column in the distillation apparatus or the evaporation apparatus. The condenser is generally classified into a condenser provided inside a column and a condenser provided outside the column, but the present invention is usually applied to the condenser provided outside the column. A type of condenser is not particularly limited, and specific examples of the condenser include a vertical fixed tube plate type, a horizontal fixed tube plate type, a U-tube type, a double-pipe type, a spiral type, a square block type, and a plate type.

Materials for the handling device, manufacturing apparatus, and peripheral devices thereof in the present invention are not particularly limited and are preferably selected depending on the easily polymerizable compound to be handled and temperature conditions. Stainless steels are often used as such materials in production of (meth)acrylic acid and (meth)acrylates which are typical easily polymerizable substances, for example, but the materials are not limited to stainless steels. Examples of such stainless steels include SUS 304, SUS 304L, SUS 316, SUS 316L, SUS 317, SUS 317L, SUS 327, and hastelloys. The materials are selected corresponding to physical properties of each liquid from a viewpoint of corrosion resistance or the like.

In the present invention, an amount of the polymerization inhibitor spread on the condensation part from a spreader for polymerization inhibitor can be arbitrarily determined depending on various conditions such as the supply amount of the easily polymerizable compound to the handling device, the type of easily polymerizable compound, and a size of the condensation part.

Hereinafter, a distillation apparatus for acrylic acid will be described in embodiments of the present invention with reference to the drawings.

First Embodiment

Figure 4:
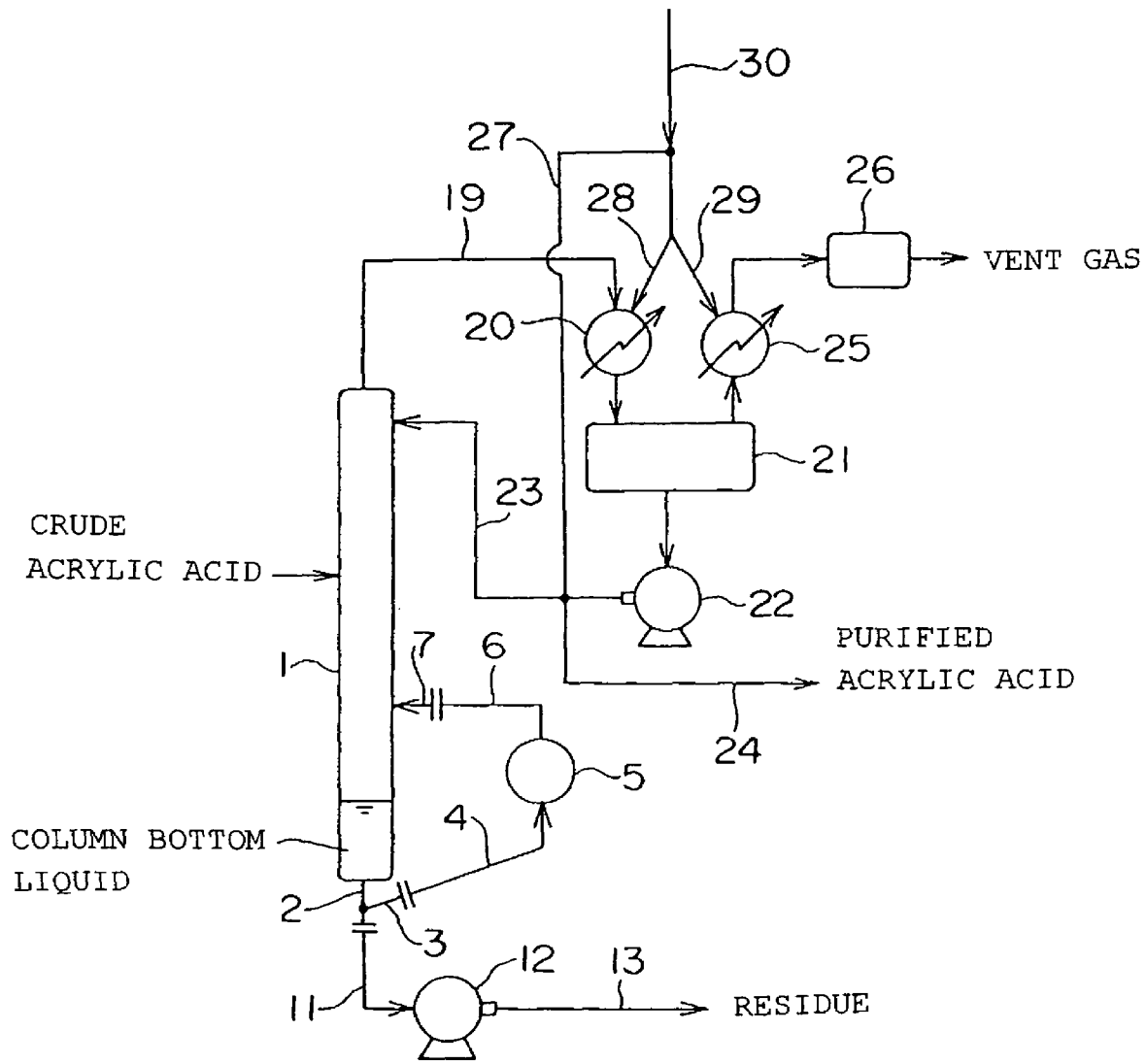
FIG. 4 is a schematic diagram of a distillation apparatus as an example of an apparatus for manufacturing according to the present invention.

As shown in FIG. 4, the distillation apparatus for acrylic acid comprises: a column body (distillation column) 1 for distilling crude acrylic acid; a condenser 20 for cooling a vapor containing acrylic acid for condensation thereof; a reflux tank 21 for receiving a condensate condensed in the condenser 20; a vent gas condenser 25 for further cooling a gas cooled in the condenser 20, to thereby recover valuable substances; and vacuum equipment 26 for making the distillation system reduce the pressure.

A draw nozzle 2 for drawing a column bottom liquid is provided in a bottom part of the column body 1. An introduction nozzle 3 and a tube 11 through which part of the drawn column bottom liquid is supplied are connected to the draw nozzle 2.

A tube 4 for delivering the column bottom liquid from the introduction nozzle 3 is connected to the introduction nozzle 3, and a reboiler 5 for heating the column bottom liquid from the tube 4 is connected to the tube 4. A tube 6 for delivering the heated column bottom liquid is connected to the reboiler 5, and a nozzle 7 for supplying the column bottom liquid to the column body 1 from the tube 6 is connected to the tube 6.

A pump 12 for delivering the column bottom liquid from the tube 11 is connected to the tube 11, and a tube 13 is connected to the pump 12.

On the other hand, a tube 19 for delivering a gas containing acrylic acid is connected to a column top part of the column body 1. The condenser 20 is connected to the tube 19, and the reflux tank 21 is connected to the condenser 20. The vent gas condenser 25 and a pump 22 for delivering the condensate in the reflux tank 21 are connected to the reflux tank 21. The vacuum equipment 26 is connected to the vent gas condenser 25.

A tube 23 for returning part of the condensate to the column body 1 is connected to the pump 22. The tube 23 is branched into a tube 24 for delivering part of the condensate as purified acrylic acid and a tube 27 for delivering part of the condensate toward the condenser 20 and the vent condenser 25.

A polymerization inhibitor supply tube 30 for supplying a polymerization inhibitor to part of the condensate is connected to the tube 27. The tube 27 is branched into a first polymerization inhibitor supply tube 28 for supplying the condensate containing the supplied-polymerization inhibitor to the condenser 20 and a second polymerization inhibitor supply tube 29 for supplying the condensate containing the supplied-polymerization inhibitor to the vent gas condenser 25.

As shown in FIG. 1, the condenser 20 is a vertical fixed tube plate-type heat exchanger in which a gas flows through tubes and a cooling medium flows through a shell. The condenser 20 includes: a tube plate 33 dividing a chamber 31 to which a gas containing acrylic acid is supplied from above and a chamber 32 to which a cooling medium is supplied; and cooling tubes 34 opening at the chamber 31 and passing through the chamber 32 vertically. Only one of the cooling tubes 34 is shown in FIG. 1, but a plurality of cooling tubes 34 are provided.

The first polymerization inhibitor supply tube 28 is inserted into the chamber 31 from the outside of the condenser 20, and a spray 35 is connected to a tip of the first polymerization inhibitor supply tube 28. The first polymerization inhibitor supply tube 28 is supported by a supporter 36 at the outside of the condenser 20. Thus, the spray 35 is supported at a position allowing spray of the polymerization inhibitor on the entire top face of the tube plate 33. The vent condenser 25 has the same structure as that of the condenser 20.

Crude acrylic acid is introduced into the column body 1 for distillation. Part of the column bottom liquid is circulated in the order of the draw nozzle 2, the introduction nozzle 3, the tube 4, the reboiler 5, the tube 6, and the nozzle 7, and is returned to the column body 1. The other part of the column bottom liquid is taken out as a residue through the draw nozzle 2, the tube 11, the pump 12, and the tube 13. A distilled substance from the top of the column is introduced into the reflux tank 21 through the tube 19 and the condenser 20. A column bottom temperature is preferably 60 to 120° C., particularly preferably 70 to 100° C., and a column top pressure is preferably 1 to 50 kPa, particularly preferably 2 to 20 kPa.

Part of acrylic acid in the reflux tank 21 is returned to the top of the column through the pump 22 and the tube 23. Other part of the acrylic acid is delivered through the tube 27 and mixed with the polymerization inhibitor supplied from the polymerization inhibitor supply tube 30. The mixture is supplied to the spray 35 provided inside each of the condenser 20 and the vent gas condenser 25 through the first polymerization inhibitor supply tube 28 and the second polymerization inhibitor supply tube 29.

A mixed solution of acrylic acid and the polymerization inhibitor is sprayed on the entire top face of the tube plate 33 from the spray 35. The tube plate 33 is cooled by the cooling medium in the chamber 32. Thus, when a gas supplied to the chamber 31 is in contact with the tube plate 33, acrylic acid in the gas is easily condensed, and a liquid of acrylic acid without the polymerization inhibitor forms on the tube plate 33. That is, the top face of the tube plate 33 serves as the condensation part.

However, acrylic acid containing the polymerization inhibitor is sprayed on the tube plate 33 and the polymerization inhibitor is supplied to the liquid of acrylic acid on the tube plate 33, thereby preventing formation of a polymerized product of acrylic acid on the tube plate 33. In the vent condenser 25, formation of a polymerized product of an easily polymerizable compound such as acrylic acid is prevented as well.

Further, the polymerization inhibitor flows into the cooling tubes 34, and the polymerization inhibitor is supplied to the condensate of acrylic acid formed inside the cooling tubes 34. Thus, formation of a polymerized product of acrylic acid is prevented in the cooling tubes 34 and the reflux tank 21, thereby preventing clogging of the cooling tubes 34 and the like.

The remaining acrylic acid from the reflux tank 22 is taken out as purified acrylic acid through the tube 24 branched from the tube 23. A gas in the reflux tank 21 is cooled again in the vent gas condenser 25, and the condensed acrylic acid is returned to the reflux tank 21. A gas component is taken out as a vent gas after passing through the vacuum equipment 26.

In the present embodiment, with a simple structure of providing the supporter 36 at the outside of the condenser 20, the first polymerization inhibitor supply tube 28 can be supported without bringing the supporter 36 into contact with a gas containing acrylic acid, thereby supporting the spray 35 at an appropriate position. Thus, formation of a condensate or polymerized product of acrylic acid on the supporter 36 can be prevented, thereby allowing a stable continuous operation of a manufacturing apparatus for manufacturing acrylic acid for a long period of time.

Second Embodiment

Figure 2:
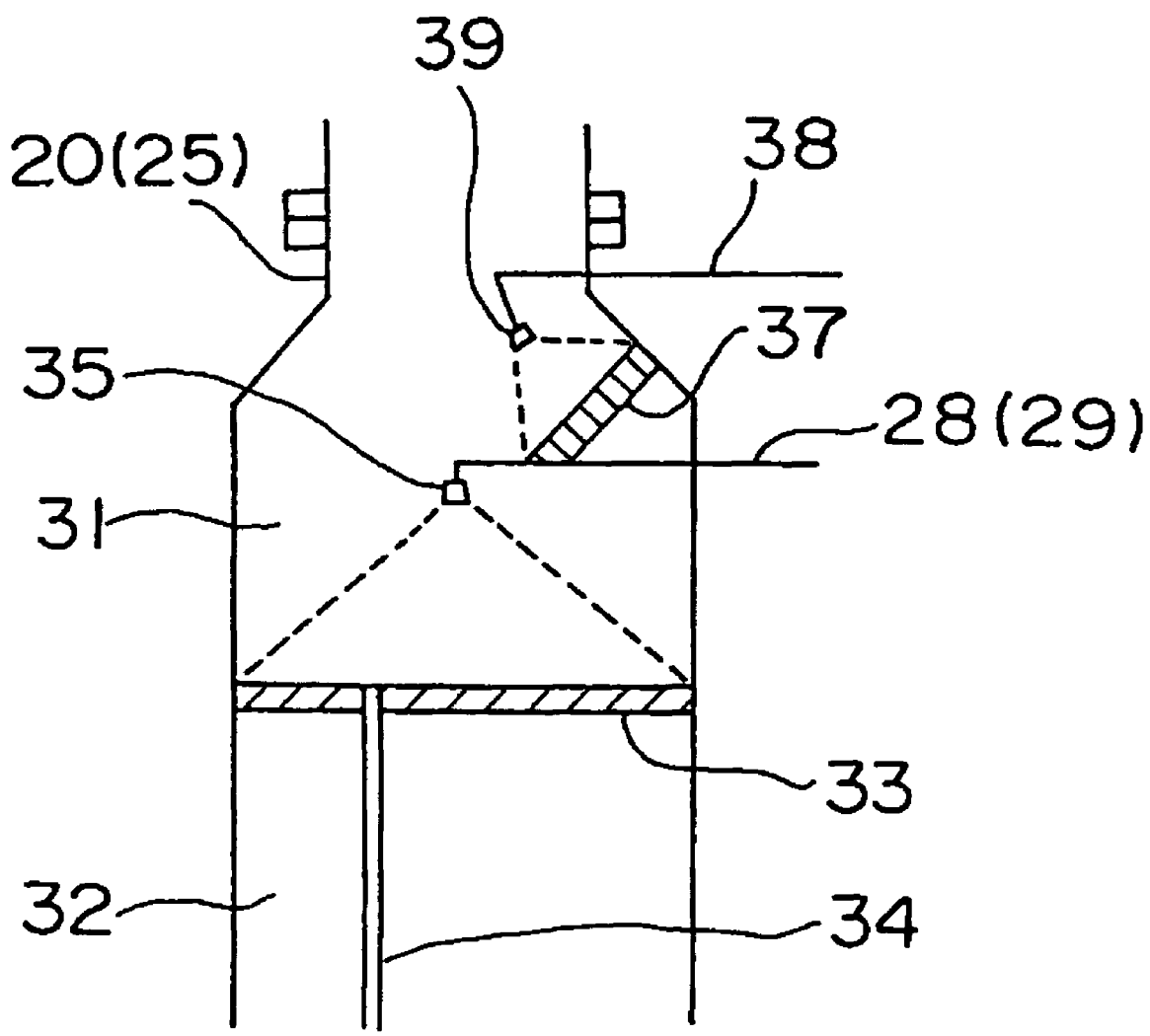
FIG. 2 is a vertical sectional view of an upper portion of a condenser according to another embodiment of the present invention.

As shown in FIG. 2, an apparatus for manufacturing acrylic acid according to the present embodiment has the same structure as that of the first embodiment except that: a supporter 37 for supporting the first polymerization inhibitor supply tube 28 inside the condenser 20 from above is used instead of the supporter 36; and a third polymerization inhibitor supply tube 38 inserted into the chamber 31 from the outside of the condenser 20 and a spray 39 connected to a tip of the third polymerization inhibitor supply tube 38 for spraying the polymerization inhibitor on the entire supporter 37 are further provided. The spray 39 is supported at a position where the polymerization inhibitor can be supplied to the entire supporter 37 by the third polymerization inhibitor supply tube 38. The third polymerization inhibitor supply tube 38 may be: a tube branched from the first polymerization inhibitor supply tube 28; a tube branched from the tube 27 downstream of a connecting part of the polymerization inhibitor supply tube 30; or a tube for supplying a polymerization inhibitor from a completely different line.

In the present embodiment, a gas containing acrylic acid brought into contact with the supporter 37 may be condensed on the surface of the supporter 37. That is, a condensation part in the present embodiment includes the surface of the supporter 37. However, the polymerization inhibitor is sprayed on the surface of the supporter 37, thereby preventing formation of a polymerized product of acrylic acid on the surface of the supporter 37.

The present embodiment allows support of the first polymerization inhibitor supply tube 28, support of the spray 35 at an appropriate position, and prevention of formation of a polymerized product of acrylic acid inside the condenser 20 even when the first polymerization inhibitor supply tube 28 is hardly supported at the outside of the condenser 20 due to various problems such as vibration prevention or strength of the tube.

In the present embodiment, employing a tube branched form the first polymerization inhibitor supply tube 28 as the third polymerization inhibitor supply tube 38 is more effective in supplying the polymerization inhibitor to the condenser 20 or the vent gas condenser 25 with a simple structure.

Third Embodiment

Figure 3:
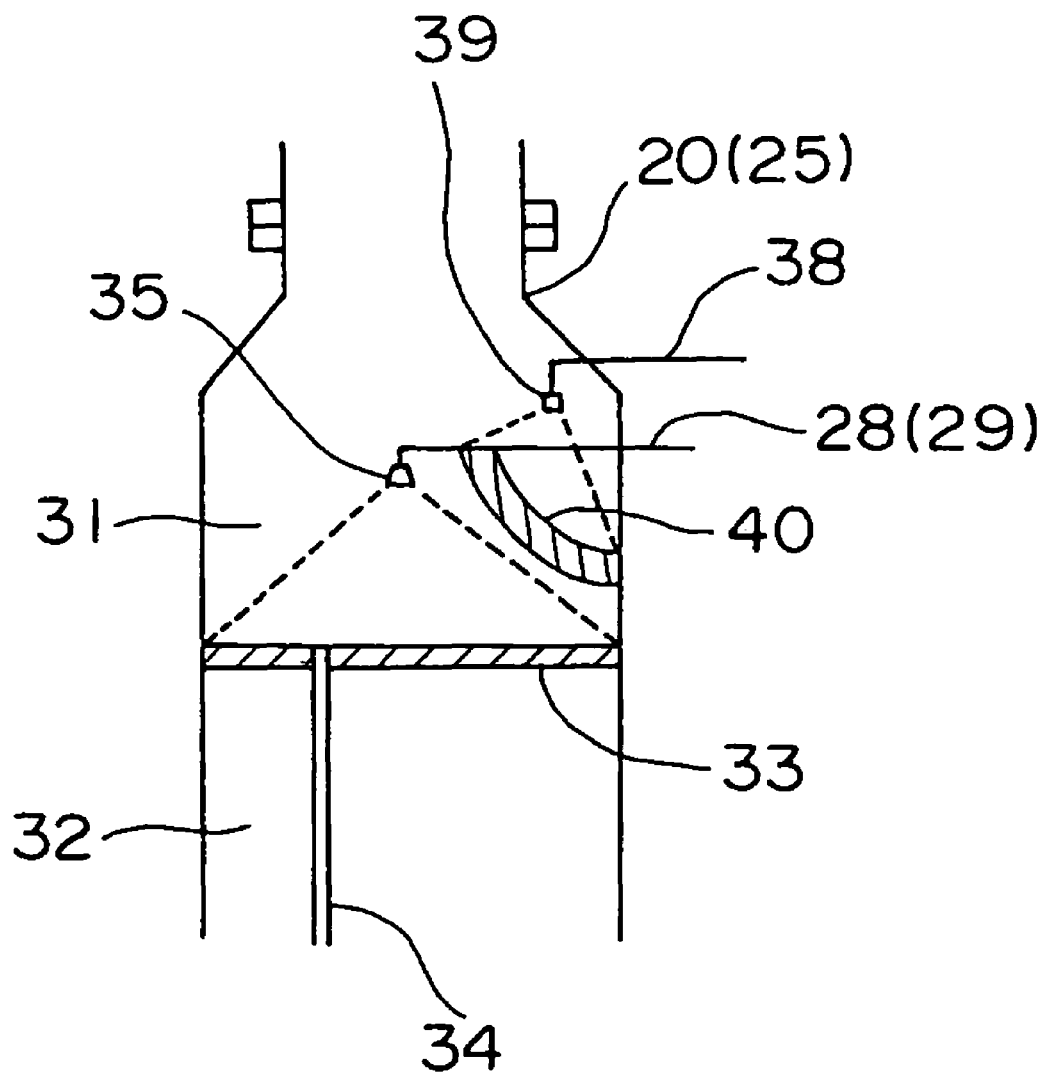
FIG. 3 is a vertical sectional view of an upper portion of a condenser according to still another embodiment of the present invention.

As shown in FIG. 3, a manufacturing apparatus for manufacturing acrylic acid according to the present embodiment has the same structure as that of the second embodiment except that: a supporter 40 for supporting the first polymerization inhibitor supply tube 28 inside the condenser 20 from below is used instead of the supporter 37; and the spray 39 is supported by the third polymerization inhibitor supply tube 38 at a position where the polymerization inhibitor can be sprayed on the entire supporter 40. The same effects as those in the second embodiment can be provided in the present embodiment.

In the present invention, a position of a supporter provided as the supporting means may be determined through mechanical strength calculations usually carried out. However, a supporter is generally provided: outside the condenser 20 when the column body 1 has a diameter of less than 1 m; and inside the condenser 20 when the column body 1 has a diameter of 1 m or more.

Further, the embodiments of the present invention each employ a supporter having a brace structure as a supporter, but the supporter used in the present invention is not limited thereto. The supporter only needs to employ "shape", "dimensions", and "thickness" provided as a result of the mechanical strength calculations usually carried out.

EXAMPLES

Hereinafter, the present invention will be described in more detail based on examples and comparative examples, but the present invention is not limited thereto.

Example 1

Distillation of crude acrylic acid was carried out in the distillation apparatus shown in FIG. 4 using the distillation column of stainless steel SUS 316 having an inner diameter of 1,100 mm, a length of 20,000 mm, and 21 perforated plates (dual flow trays) provided thereinside as the column body 1. The condenser 20 of SUS 316L had a diameter of 890 mm and a length of 3,050 mm. The vent condenser 25 of SUS 316L had a diameter of 480 mm and a length of 2,440 mm. A condensate flows through the cooling tubes in each of the condenser 20 and the vent gas condenser 25.

The spray 35 was provided inside each of the condenser 20 and the vent gas condenser 25, and the supporter was not provided thereinside as shown in FIG. 1.

In the distillation apparatus shown in FIG. 4, a mixture containing 98.5% by mass acrylic acid, 0.3% by mass maleic acid, and 0.3% by mass acrylic acid dimer as crude acrylic acid was supplied to the column body 1 at 90° C. and 1,300 kg/h.

A liquid prepared by dissolving 8% by mass methoquinone and 1% by mass phenothiazine in acrylic acid was supplied to the column top of the column body 1 at 34 kg/h and to the crude acrylic monomer liquid supplied to the column body 1 at 31 kg/h, from a not-shown polymerization inhibitor-containing liquid tank. An operation was carried out at a column top pressure of 2.8 kPa, a column bottom pressure of 7.9 kPa, a column top temperature of 53° C., and a column bottom temperature of 75° C., to thereby obtain high purity acrylic acid having a purity of 99.8% by mass or more from the column top.

Part of the high purity acrylic acid obtained from the column top was adjusted to a methoquinone concentration of 200 ppm by mass by mixing with a liquid containing a polymerization inhibitor (methoquinone) from the polymerization inhibitor supply tube 30 through the condenser 20, the reflux tube 21, the pump 22, and the tube 27. The adjusted high purity acrylic acid was supplied to the condenser 20 at 1,020 kg/h and to the vent gas condenser 25 at 995 kg/h.

After a continuous operation for 6 months under the above-mentioned conditions, the operation was stopped for an inspection of the condenser 20 and the column body 1. The results of the inspection confirmed: no accumulated substances; and no clogging of the condenser 20 during the operation.

Comparative Example 1

Figure 5:
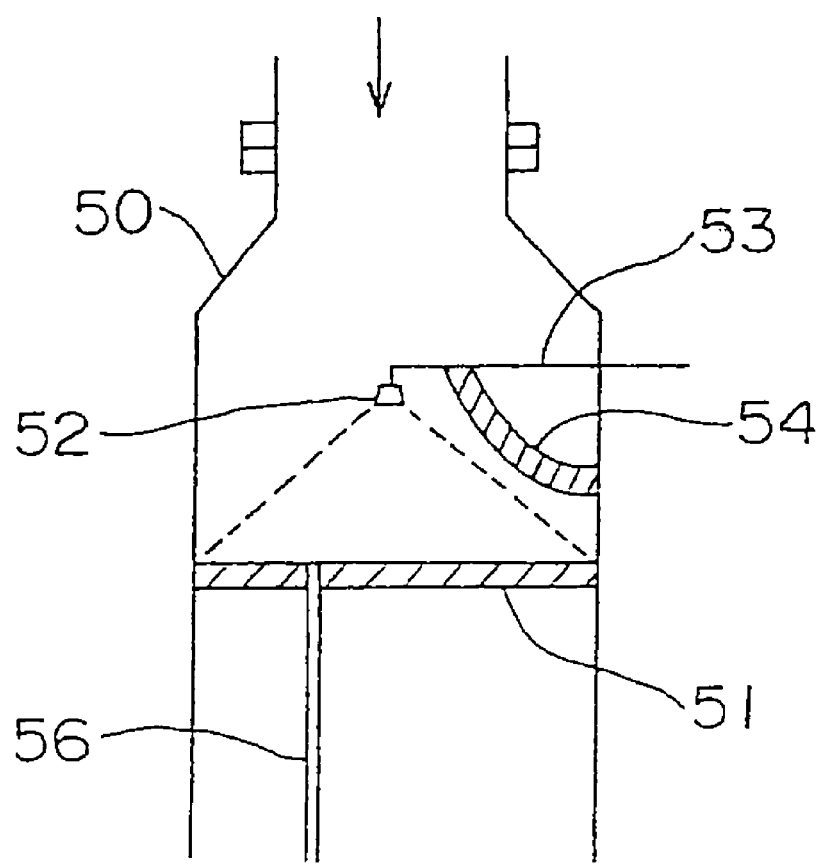
FIG. 5 is a vertical sectional view of an upper portion of an example of a conventional condenser.

The same operation was repeated as that in Example 1 except that the condenser 20 and the vent gas condenser 25 shown in FIG. 1 were replaced by the condenser 50 shown in FIG. 5.

After an operation for 3 months, a temperature of the column bottom liquid gradually increased, and a difference between a pressure of the reflux tank 21 and a column top pressure of the column body 1 increased. Thus, a steam could not be supplied to the reboiler 5.

The operation was stopped, and the inside of the apparatus was inspected. The result of the inspection confirmed a pop-corn-like polymerized product on the top face of the tube plate 51 in the condenser 50.

Example 2

Distillation of crude ethyl acrylate was carried out in the distillation apparatus shown in FIG. 4 using the distillation column of stainless steel (SUS 316) having an inner diameter of 1,500 mm, a length of 14,700 mm, and 20 dual flow trays provided thereinside. The condenser 20 of SUS 316L had a diameter of 1,020 mm and a length of 3,050 mm. The vent condenser 25 of SUS 316L had a diameter of 303 mm and a length of 2,440 mm. A condensate flows through the cooling tubes in each of the condenser 20 and the vent gas condenser 25.

The spray 35 was provided inside each of the condenser 20 and the vent gas condenser 25, and the supporter was not provided thereinside as shown in FIG. 1.

In the distillation apparatus shown in FIG. 4, a mixture containing 99.3% by mass ethyl acrylate, 0.04% by mass ethyl acetate, 0.04% by mass ethyl propionate, 0.52% by mass acrylic acid, and 0.1% by mass hydroquinone as crude acrylate was supplied to the column body 1 at 90° C. and 4,500 kg/h.

A liquid prepared by dissolving 1.5% by mass methoquinone in ethyl acrylate was supplied to the column top of the column body 1 at 30 kg/h from the polymerization inhibitor-containing liquid tank (not shown). An operation was carried out at a column top pressure of 21.3 kPa, a column bottom pressure of 26.7 kPa, a column top temperature of 56° C., and a column bottom temperature of 71° C., to thereby obtain high purity ethyl acrylate having a purity of 99.9% by mass or more from the column top.

Part of the high purity ethyl acrylate obtained from the column top was mixed with 11 kg/h of a liquid containing a polymerization inhibitor from the polymerization inhibitor supply tube 30 through the condenser 20, the reflux tube 21, the pump 22, and the tube 27. The mixture was supplied to the condenser 20 at 1,750 kg/h and to the vent gas condenser 25 at 1,000 kg/h.

After a continuous operation for 6 months under the above-mentioned conditions, the operation was stopped for an inspection of the condenser 20 and the column body 1. The results of the inspection confirmed: no accumulated substances; and no clogging of the condenser 20 during the operation.

Comparative Example 2

Figure 6:
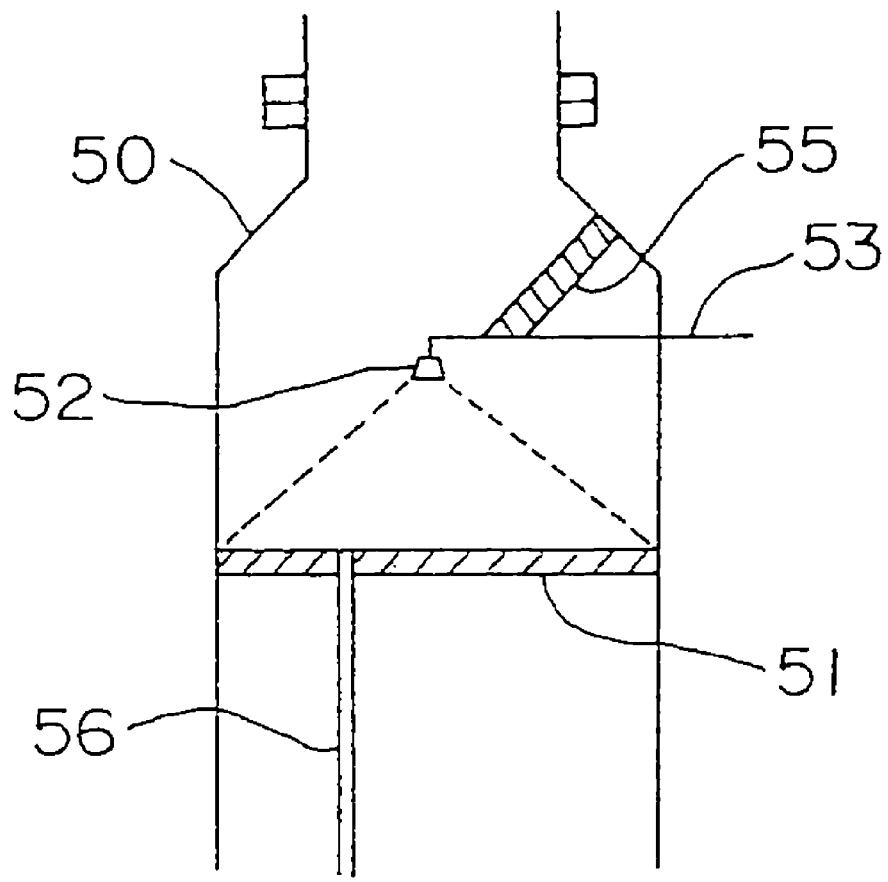
FIG. 6 is a vertical sectional view of an upper portion of another example of a conventional condenser.

The same operation was repeated as that in Example 2 except that the condenser 20 and the vent gas condenser 25 shown in FIG. 1 were replaced by the condenser 50 shown in FIG. 6.

After an operation for 4 months, a temperature of the column bottom liquid gradually increased, and a difference between a pressure of the reflux tank 21 and a column top pressure of the column body 1 increased. Thus, a steam could not be supplied to the reboiler 5.

The operation was stopped, and the inside of the apparatus was inspected. The result of the inspection confirmed a polymerized product on the top face of the tube plate 51 in the condenser 50.

INDUSTRIAL APPLICABILITY

According to the present invention, formation of a polymerized product due to a support means provided for spreading of a polymerization inhibitor is suppressed in a handling device for handling an easily polymerizable compound such as a condenser or a vent gas condenser, thereby preventing clogging. Thus, a manufacturing apparatus for manufacturing an easily polymerizable compound such as distillation column equipment including the handling device for an easily polymerizable compound can be stably and continuously operated for a long period of time.

The present invention is more effective for spreading the polymerization inhibitor extensively and efficiently when the spreader for spreading the polymerization inhibitor is a spray.

In particular, the present invention is more effectively applied to handling or production of an easily polymerizable compound such as (meth)acrylic acid or (meth)acrylate.

The invention claimed is:

1. A device for handling an easily polymerizable compound into which a vapor of the easily polymerizable compound is supplied, comprising:
    a condensation part in which the easily polymerizable compound may be condensed inside the device;
    a spreader for the condensation part that spreads a polymerization inhibitor on the condensation part;
    a polymerization inhibitor supply tube that supplies the polymerization inhibitor to the spreader for the condensation part; and
    a support means for supporting the polymerization inhibitor supply tube outside the device so that the spreader for the condensation part is supported at a predetermined position inside the device, wherein
    the polymerization inhibitor supply tube passes through an outer wall of the device,
    the support means is provided between the outer wall of the device and a lower portion of the polymerization inhibitor supply tube, and
    the support means extends away from the outer wall of the device in a substantially upwards direction.

2. The device for handling an easily polymerizable compound according to claim 1, wherein the device is a condenser.

3. The device for handling an easily polymerizable compound according to claim 1, wherein the spreader is a spray.

4. The device for handling an easily polymerizable compound according to claim 1, wherein the easily polymerizable compound is selected from a group consisting of (meth)acrylic acid and (meth)acrylate.

5. An apparatus for manufacturing an easily polymerizable compound comprising a device for handling an easily polymerizable compound, wherein:
    the device is the device for handling an easily polymerizable compound according to claim 1.

6. The apparatus for manufacturing an easily polymerizable compound according to claim 5, wherein the apparatus is a distillation apparatus or evaporation apparatus for an easily polymerizable compound.

7. The apparatus for manufacturing an easily polymerizable compound according to claim 5, wherein the easily polymerizable compound is selected from a group consisting of (meth)acrylic acid and (meth)acrylate.

8. A device for handling an easily polymerizable compound into which a vapor of the easily polymerizable compound is supplied, comprising:
    a condensation part in which the easily polymerizable compound may be condensed inside the device;
    a spreader for the condensation part that spreads a polymerization inhibitor on the condensation part;
    a first polymerization inhibitor supply tube that supplies the polymerization inhibitor to the spreader for the condensation part; and
    a support means for supporting the first polymerization inhibitor supply tube at the inside of the device so that the spreader for the condensation part is supported at a predetermined position inside the device,
    wherein the device further includes a spread means for the support means for spreading the polymerization inhibitor on the support means.

9. The device for handling an easily polymerizable compound according to claim 8, wherein the device is a condenser.

10. The device for handling an easily polymerizable compound according to claim 8, wherein the spreader is a spray.

11. The device for handling an easily polymerizable compound according to claim 8, wherein the easily polymerizable compound is selected from a group consisting of (meth)acrylic acid and (meth)acrylate.

12. An apparatus for manufacturing an easily polymerizable compound comprising a device for handling an easily polymerizable compound, wherein:
    the device is the device for handling an easily polymerizable compound according to claim 8.

13. The apparatus for manufacturing an easily polymerizable compound according to claim 12, wherein the apparatus is a distillation apparatus or evaporation apparatus for an easily polymerizable compound.

14. The apparatus for manufacturing an easily polymerizable compound according to claim 12, wherein the easily polymerizable compound is selected from a group consisting of (meth)acrylic acid and (meth)acrylate.

15. The device for handling an easily polymerizable compound according to claim 8, wherein the spread means is supplied the polymerization inhibitor via a second polymerization inhibitor supply tube that is provided separately from the first polymerization inhibitor supply tube.

16. The device for handling an easily polymerizable compound according to claim 15, wherein the spread means is a secondary spray located above the support means such that the spread means sprays the polymerization inhibitor over the support means in entirety.

* * * * *

UNITED STATES PATENT AND TRADEMARK OFFICE
CERTIFICATE OF CORRECTION

PATENT NO. : 7,892,403 B2  Page 1 of 1
APPLICATION NO. : 11/578237
DATED : February 22, 2011
INVENTOR(S) : Shuhei Yada et al.

It is certified that error appears in the above-identified patent and that said Letters Patent is hereby corrected as shown below:

On the title page, Item (54), and column 1, the title is incorrect. Item (54) and column 1 should read:

-- DEVICE FOR HANDLING EASILY POLYMERIZABLE COMPOUND AND APPARATUS FOR MANUFACTURING EASILY POLYMERIZABLE COMPOUND --

Signed and Sealed this
Fourteenth Day of June, 2011

David J. Kappos
*Director of the United States Patent and Trademark Office*